United States Patent [19]

Carroll et al.

[11] 4,011,231

[45] Mar. 8, 1977

[54] 2-PHENYL-6-(1-HYDROXY-2-t-BUTYLAMINOETHYL)-4H-PYRIDO[3,2-d]-1,3-DIOXIN MALEATE AND ITS USE AS AN INTERMEDIATE

[75] Inventors: Ronnie D. Carroll, East Lyme; Bernard S. Moore, Waterford; James R. Tretter, Niantic, all of Conn.

[73] Assignee: Pfizer Inc., New York, N.Y.

[22] Filed: Oct. 3, 1975

[21] Appl. No.: 619,302

[52] U.S. Cl. .......................... 260/296 R; 424/263; 260/297 B

[51] Int. Cl.² ...................................... C07D 213/69

[58] Field of Search ....... 260/296 R, 296 H, 296 V, 260/295.5 V, 297, 296 R

[56] References Cited

UNITED STATES PATENTS 3,250,778 5/1966 Kimel et al. ................... 260/297 V

FOREIGN PATENTS OR APPLICATIONS 823,616 6/1975 Belgium

OTHER PUBLICATIONS

Nakanishi et al., Chemical Abstracts vol. 77, abst. 5492m (1972) (abst. of Japanese Patent 47–03832).
Ratle et al., Bull. Soc. Chim. France 1966, pp. 2945 to 2947.

*Primary Examiner*—John D. Randolph
*Attorney, Agent, or Firm*—Connolly and Hutz

[57] ABSTRACT

The maleic acid salt of 2-phenyl-6-(1-hydroxy-2-t-butylaminoethyl)-4H-pyrido[3,2-d]-1,3-dioxin, its preparation and use as an intermediate for making 2-hydroxymethyl-3-hydroxy-6-(1-hydroxy-2-t-butylaminoethyl)pyridine, an effective bronchodilator.

1 Claim, No Drawings

2-PHENYL-6-(1-HYDROXY-2-t-BUTYLAMINOE- THYL)-4H-PYRIDO[3,2-d]-1,3-DIOXIN MALEATE AND ITS USE AS AN INTERMEDIATE

BACKGROUND OF THE INVENTION

1. Field of the Invention

This invention relates to an acid addition salt of 2-phenyl-6-(1-hydroxy-2-t-butylaminoethyl)-4H-pyrido[3,2-d]-1,3-dioxin and to a process for its preparation. More specifically, it relates to the maleic acid salt of said compound, and to a process for its preparation, particularly in crystalline form.

2. Description of the Prior Art

Belgian Patent 823,616, granted June 20, 1975, describes the preparation of 2-hydroxymethyl-3-hydroxy-6-(1-hydroxy-2-t-butylaminoethyl)-pyridine (formula IV), a bronchodilator, by the following three related sequences:

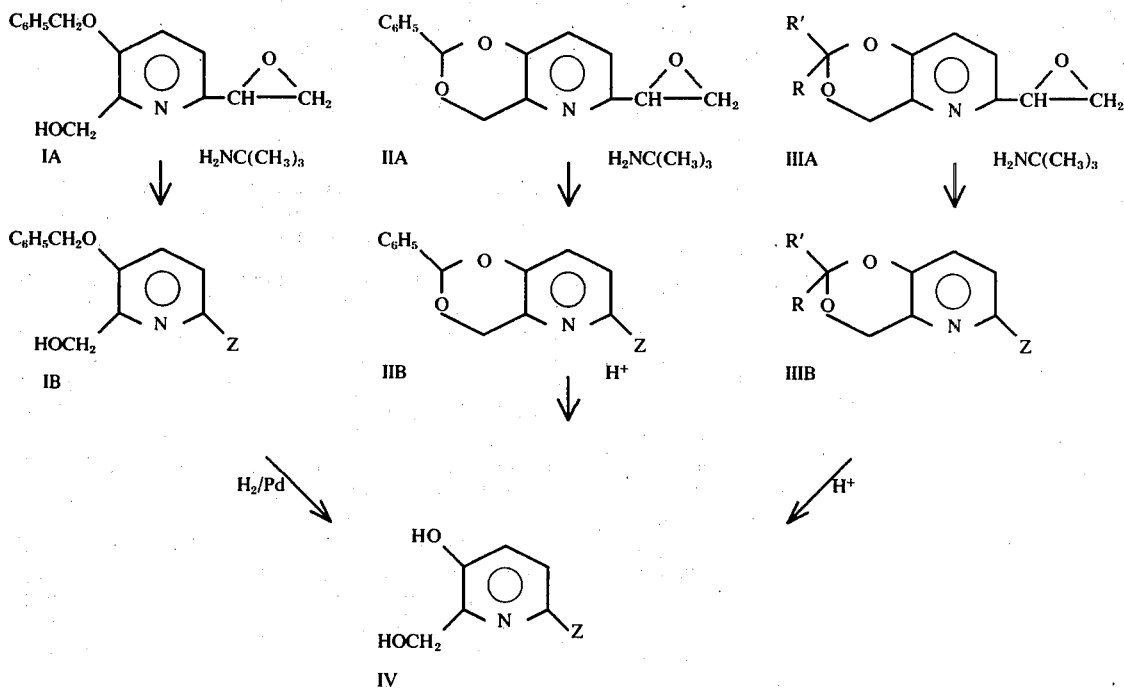

In the above formulae, each of R and R' is phenyl or methyl; and Z is —CHOH—CH$_2$—NH—C(CH$_3$)$_3$.

The reaction sequence IA → IB → IV affords good yields of the final product (IV) but suffers from the economic disadvantage of requiring catalytic hydrogenation to remove the benzyl group. Further, preparation of the starting benzyl ether (IA) requires benzyl bromide, a relatively expensive substance, as reactant.

Reaction sequence IIIA → IIIB → IV is less attractive from an economic standpoint than is sequence IIA → IIB → IV because of the relatively high costs realized in the preparation of reactant IIIA.

The sequence IIA → IIB → IV is free of the above disadvantages. However, on large scale operation it, as are the other two sequences, is subject to formation of colored impurities in the amination step. Its presence, along with that of other substances, coupled with the fact that for convenience and economy of large scale operation the intermediates are not purified, leads to formation of colored impurities. In sequence IIA → IIB → IV these impurities interfere in the isolation, recovery and purification of intermediate IIB and final product IV. The impurities appear to arise, in part at least, from the presence of iodide introduced via trimethylsulfonium iodide in the preparation of the epoxides (IA, IIA, IIIA).

SUMMARY OF THE INVENTION

The process of the present invention is a modification of the sequence IIA → IIB → IV described in Belgian Patent 823,616 and one which achieves substantial improvement in yield and purity in the large scale preparation of the final product 2-hydroxymethyl-3-hydroxy-6-(1-hydroxy-2-t-butylaminoethyl)pyridine (formula IV) when prepared by this route. Increased economic advantage of this route over the other two routes described therein is realized. The process comprises converting the acetal-amine, 2-phenyl-6-(1-hydroxy-2-t-butylaminoethyl)-4H-pyrido[3,2-d]-1,3-dioxin (IIB), to its maleate salt prior to its transformation, by acid treatment, to 2-hydroxymethyl-3-hydroxy-6-(1-hydroxy-2-t-butylaminoethyl)pyridine.

DETAILED DESCRIPTION OF THE INVENTION

The conversion of the acetal-amine (IIB) to its maleate salt is accomplished by reacting it, in ethyl acetate solution, with a solution of maleic acid in ethyl acetate. The molar ratio of acetal-amine to maleic acid should be at least about 1:1. In actual practice, molar ratios of acetalamine to maleic acid of from about 1:1 to about 1:1.5 are generally used. Molar ratios of maleic acid greater than 1.5 per mole of acetal-amine give rise to separation of excess maleic acid along with the desired maleate salt and are, therefore, not used. A favored ratio of acetal-amine to maleic acid is 1:1.2, since it affords satisfactory yields of high quality maleate salt.

The process permits use of crude acetal-epoxide, 2-phenyl-4H-pyrido-[3,2-d]-1,3-dioxin-6-epoxyethane (IIA) in the large scale overall process leading to formation of final product (IV). In so doing, it achieves greater economic advantage over the other processes of Belgian 823,616 not only by eliminating the need for purifying the acetal-epoxide, but also by producing an acetal-amine of higher purity and greater yield.

A variety of solvents can be used in the process of this invention for forming the maleate salt. Included among operable solvents are ethyl acetate, ethyl propionate, propyl acetate, acetonitrile, acetone, methanol and ethanol. Among the several solvents enumerated above, ethyl acetate is preferred since it affords the maleate salt in crystalline form of high quality and in satisfactory yield.

Formation of the maleate salt can be carried out over a wide temperature range; eg., from about 20° C. to the boiling point of the solvent, ethyl acetate. The favored temperature range is from about 30° C. to about 50° C. In actual practice a temperature of from about 35° C. to 42° C. is used since it permits use of homogeneous solutions, convenient volume of solvent and affords optimum yield and quality of product.

The maleate salt thus produced can be used as is to produce 2-hydroxymethyl-3-hydroxy-6-(1-hydroxy-2-t-butylaminoethyl)pyridine. It can, if desired, be purified by dissolution in hot methanol and decoloration of the solution. Removal of the methanol solvent and addition of ethyl acetate to the residue affords the pure maleate salt.

The final product, 2-hydroxymethyl-3-hydroxy-6-(1-hydroxy-2-t-butylaminoethyl)pyridine, is generally employed as the dihydrochloride salt. Transformation of the acetal-amine maleate to the dihydrochloride salt of the final product (IV) is readily accomplished by reacting the maleate salt with an excess of hydrogen chloride. A preferred procedure comprises adding the acetal-amine maleate to methanolic-hydrogen chloride in a molar ratio of maleate salt to HCl of from about 1:3 to about 1:6, and desirably at about 1:4, at a temperature of about 20° C. to 25° C. From about 2–3 liters of methanol per mole of maleate salt is used. The mixture is stirred until conversion is complete, about 2 hours, and is then concentrated; e.g., to approximately one-fourth its original volume, under reduced pressure, and the resulting concentrate diluted with a large volume of acetone. The dihydrochloride salt of the final product precipitates, and, after granulating at about 25° C., for 0.5 to 1.0 hour, is recovered by filtration or other suitable means.

In addition to maleic acid, other organic acids, such as fumaric, tartaric, citric and malic acids, can be used to purify and isolate the intermediate acetal-amine. The organic salt is then converted to the dihydrochloride salt of the final product (IV) in the same manner as is the maleate salt.

EXAMPLE 1

2-Phenyl-6-(1-hydroxy-2-t-butylaminoethyl)-4H-pyrido[3,2-d]-1,3-dioxin Maleate (From Crude Acetal-Epoxide)

A pressure reactor is purged with nitrogen and charged with 2-phenyl-4H-pyrido[3,2-d]-1,3-dioxin-6-epoxyethane (12.672 kg., 49.6 moles) and t-butylamine (59.2 kg., 810 moles). The reactor is then pressurized to 30 p.s.i. with nitrogen and heated and stirred at 80° C. for 28 hours. The reactor is then cooled to 20° C. and allowed to stand overnight. The reaction mixture is concentrated under reduced pressure to about 25 liters volume. Benzene (95 liters) is added to the oily concentrate and the resulting solution concentrated to about 25–30 liters volume under reduced pressure. A second charge of benzene (95 liters) is added to the concentrate and the solution concentrated to about 25 liters volume. To the residue of acetal-amine, a thick slurry, ethyl acetate (45 liters) is added and the mixture heated to 40° C. to dissolve the slurry. A solution of maleic acid (7.0 kg., 60 moles) in ethyl acetate (135 liters) at 40° C. is added to the acetal-amine solution to precipitate the crystalline maleate salt. The mixture is stirred for one hour and is then cooled to 25° C. After stirring at 25° C. for 1 hour, the crystalline maleate salt is recovered by filtration, washed with ethyl acetate (60 liters) and dried. Yield 13.3 kg., 60.0%. M.P. 192°–195° C. (dec.).

It is purified by dissolution in methanol (208 liters) at 50° C. and decolorization of the solution with activated charcoal. Concentration of the decolorized solution, including 38 liters of methanol washed solution from washing the charcoal filter cake, to small volume followed by addition of ethyl acetate (200 liters) precipitates the purified salt. It is filtered, washed with ethyl acetate and dried. M.P. 195°–196.5° C. Yield 12.3 kg.

Analysis: Ca.c'd for $C_{23}H_{28}N_2O_7$: C, 62.15; H, 6.35; N, 6.30%, Found: C, 62.21; H, 6.32; N, 6.38%

EXAMPLE 2

2-Phenyl-6-(1-hydroxy-2-t-butylaminoethyl)-4H-pyrido[3,2-d]-1,3-dioxin Maleate (From Crude Acetal-Epoxide)

A pressure reactor is purged with nitrogen and charged with 2-phenyl-4H-pyrido[3,2-d]-1,3-dioxin-6-epoxyethane (13.53 kg., 53 moles) and t-butylamine (62.7 kg., 859 moles). The reactor is then pressurized to 30 p.s.i. with nitrogen and heated and stirred at 80° C. for 28 hours. The reactor is then cooled to 10° C. and allowed to stand overnight. The reaction mixture is concentrated under reduced pressure to about 38 liters volume. Benzene (102 liters) is added to the oily concentrate and the resulting solution concentrated to about 30–35 liters volume under reduced pressure. A second charge of benzene (102 liters) is added to the concentrate and the solution concentrated to about 25 liters volume. To the residue of acetal-amine, a thick slurry, ethyl acetate (57 liters) is added and the mixture heated to 40° C. to dissolve the slurry. A solution of maleic acid (7.424 kg., 64 moles) in ethyl acetate (144 liters) at 40° C. is added to the acetal-amine solution to precipitate the crystalline maleate salt. The mixture is stirred for 1 hour and is then cooled to 25° C. After stirring at 25° C for 1 hour, the crystalline maleate salt is recovered by filtration, washed with ethyl acetate (60 liters) and dried. Yield = 16.1 kg., 68.3%. M.P. 176°–180° C. (dec.).

EXAMPLE 3

2-Hydroxymethyl-3-hydroxy-6-(1-hydroxy-2-t-butylaminoethyl)-pyridine Dihydrochloride (Via Maleate Salt of Acetal-Amine)

To a solution of methanol (11.3 l.)--hydrogen chloride gas (620 g., 17 moles) at 20° C. is added, with stirring, 2-phenyl-6-(1-hydroxy-2-t-butylaminoethyl)-4-H-pyrido-[3,2-d]-1,3-dioxin maleate (1880 g., 4.24 moles) over a five minute period. The resulting solution is then stirred for 2 hours at 20°–25° C. and is then concentrated under reduced pressure to a volume of about 3 liters. Acetone (16 liters) is added to the concentrate and the resulting precipitate granulated at 25°

C. for a half-hour. The white crystalline solid is separated by filtration and washed with acetone (4 liters). Yield = quantitative. M.P. 183°–187° C. (dec.).

EXAMPLE 4

2-Hydroxymethyl-3-hydroxy-6-(1-hydroxy-2-t-butylaminoethyl)-pyridine Dihydrochloride (Via Direct Conversion from Acetal-Amine)

A solution of methanolic-hydrogen chloride (27.4 g. HCl gas in 400 ml.) and 2-phenyl-6-(1-hydroxy-2-t-butylaminoethyl)-4H-pyrido[3,2-d]-1,3-dioxin (112.3 g.) is stirred at 25° C. for 3.5 hours. Acetone (2.4 liters) is added to the reaction mixture over a period of 15 minutes. A dark colored oil forms. The mixture is concentrated under reduced pressure to give a slurry. Acetone (1.5 liters) is added and the slurry granulated for a half-hour at room temperature. The tan solid, plus some darker brown lumps, is filtered and dried (72.8 g.). The solid is dissolved in methanol (300 ml.), treated with activated charcoal and filtered. The charcoal is washed with methanol (50 ml.) and the combined filtrate and wash diluted with acetone (1.5 liters). The resulting hazy solution is stirred for one hour and the off-white precipitate produced is filtered, washed with acetone and dried (59 g., 55.1%). M.P. 176°–182° (dec.).

What is claimed is:
1. A process for producing 2-hydroxymethyl-3-hydroxy-6-(1-hydroxy-2-t-butylaminoethyl)-pyridine dihydrochloride which comprises the steps of
   1. heating 2-phenyl-4H-pyrido-[3,2-d]-1,3-dioxin-6-epoxyethane with at least a molar amount of t-butylamine to obtain 2-phenyl-6-(1-hydroxy-2-t-butylaminoethyl)-4H-pyrido[3,2-d]-1,3-dioxin as product,
   2. reacting maleic acid with the product of step (1) in a molar ratio of at least 1:1 in ethyl acetate at a temperature of from 30° to 50° C. to obtain 2-phenyl-6-(1-hydroxy-2-butylaminoethyl)-4H-pyrido[3,2-d]-1,3-dioxin maleate as product and
   3. treating the product of step (2) with excess hydrochloride in methanol to obtain the desired product.

* * * * *